1

United States Patent
Hamboly

(10) Patent No.: US 8,257,298 B2
(45) Date of Patent: Sep. 4, 2012

(54) MULTITUBE CATHETER

(76) Inventor: M. Samy Ahmed Hamboly, Ramadan (EG)

( * ) Notice: Subject to any disclaimer, the term of this patent is extended or adjusted under 35 U.S.C. 154(b) by 0 days.

(21) Appl. No.: 12/711,015

(22) Filed: Feb. 23, 2010

(65) Prior Publication Data

US 2010/0152710 A1   Jun. 17, 2010

Related U.S. Application Data

(62) Division of application No. 10/905,787, filed on Jan. 20, 2005, now Pat. No. 7,740,780.

(51) Int. Cl.
*A61M 1/00* (2006.01)
(52) U.S. Cl. ............. 604/27; 604/43; 604/523; 604/264
(58) Field of Classification Search ............. 604/43–45, 604/27, 29, 264, 523
See application file for complete search history.

(56) References Cited

U.S. PATENT DOCUMENTS

| | | | |
|---|---|---|---|
| 4,411,654 A | 10/1983 | Boarini | |
| 5,180,372 A | 1/1993 | Vegoe | |
| 5,360,397 A * | 11/1994 | Pinchuk | 604/27 |
| 5,718,692 A | 2/1998 | Schon | |
| 5,776,111 A | 7/1998 | Tesio | |
| 5,947,953 A | 9/1999 | Ash et al. | |
| 6,001,079 A | 12/1999 | Pourchez | |
| 6,190,349 B1 | 2/2001 | Ash | |
| 6,524,302 B2 * | 2/2003 | Kelley | 604/523 |
| 6,695,832 B2 * | 2/2004 | Schon et al. | 604/544 |
| 6,758,836 B2 | 7/2004 | Zawacki | |
| 2004/0054321 A1 | 3/2004 | Schon | |
| 2004/0059314 A1 | 3/2004 | Schon | |
| 2004/0075198 A1 | 4/2004 | Schweikert | |
| 2004/0092863 A1 | 5/2004 | Raulerson | |

* cited by examiner

*Primary Examiner* — Theodore Stigell
(74) *Attorney, Agent, or Firm* — Decker Jones, et al.; Brian K. Yost; Geoffrey A. Mantooth

(57) ABSTRACT

A multitube catheter is provided. The assembly includes two or more tubes fused together to form one catheter tube shaft. Each tube has at least one lumen extending longitudinally through the catheter from its distal end to its proximal end. The tubes are fused together by use of heat and pressure. A distal end of the united catheter tube can be split to form a split tip, stepped tip, or a tapered tip. The proximal segment (non-fused portion) forms catheter extension legs.

18 Claims, 4 Drawing Sheets

MULTITUBE CATHETER

This application is a divisional patent application of application Ser. No. 10/905,787 filed Jan. 20, 2005, which was granted a patent on Jun. 22, 2010, U.S. Pat. No. 7,740,780.

FIELD OF THE INVENTION

The present invention relates generally to multitube catheter assemblies, and more particularly to multitube catheter assemblies having distal split independent free floating tip end, a stepped tip end, or a tapered tip end for positioning within an area to be catheterized The lumens of the multitube catheter are fully circular where they extend through the distal end, the catheter main stem and the proximal end of the extension part.

The presented multitube catheter may be used in any medical field where access to the central venous system is required like haemodialysis, haemofiltration, plasma exchange, chemotherapy infusion, etc.

BACKGROUND OF THE INVENTION

(A) Technical Background

Catheters for the introduction or removal of fluids may be located in various venous locations and cavities throughout the body for the introduction or removal of fluids. Such catheterization may be performed by using a single catheter having multiple lumens. A typical example of a multiple lumen catheter is a dual lumen catheter in which one lumen introduces fluids and one lumen removes fluids. Catheterization may also be performed by using separate, single lumen catheters inserted through two different incisions into an area to be catheterized. Procedures are also known as described for inserting two wholly independent single lumen catheters into a vessel through a single insertion site. (Such multiple catheter assemblies are known traded as Tesio catheters U.S. Pat. No. 5,776,111)

Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through a syringe needle or other introducer device, into the interior of the vessel. The introducer device is then removed leaving the guide wire within the vessel. The guide wire projects beyond the surface of the skin.

At this point, several options are available to a physician for catheter placement. The simplest is to pass a catheter into the vessel directly over the guide wire. The guide wire is then removed leaving the catheter in position within the vessel. However, this technique is only possible in cases where the catheter is of a relatively small diameter, made of a stiff material and not significantly larger than the guide wire, for example, for insertion of small diameter dual lumen catheters. If the catheter to be inserted is significantly larger than the guide wire, a dilator device is first passed over the guide wire to enlarge the hole. The catheter is then passed over the guide wire, and the guide wire and dilator are removed.

In the case of an individual, soft single-lumen catheter typically used in multiple catheter assemblies, a physician may use an introducer sheath. For Haemodialysis, for example, each catheter may be inserted into two separate veins, such as the femoral vein. Alternatively, each catheter may be inserted in two different locations of the same vein, such as the internal jugular vein as noted above. The introducer sheath is simply a large, stiff thin-walled tube, which serves as a temporary conduit for the permanent catheter which is being placed. Tear away sheaths are also available which split apart for easier removal. The introducer sheath is positioned by placing a dilator device inside of the introducer and passing both the dilator and the introducer together into the vessel over a guide wire. The guide wire, left in the vessel after insertion as described above, and the dilator are then removed, leaving the thin-walled introducer sheath in place. The catheter is placed through the introducer sheath. Each of the catheters in the assembly is typically subcutaneously secured within the patient's body by a cuff located in a subcutaneous tunnel, or by otherwise externally affixing the catheter to the body.

The single lumen catheter may also be inserted, as noted above, through a single insertion point using a sheath into the vessel. The catheter, once inserted in the vessel, is then tunneled separately through the patient in two subcutaneous tunnels for securement of the external, proximal portions of the catheter.

The double catheter assembly, while comfortable for the patient, due to its soft durometer, and very effective for Haemodialysis, typically requires multiple procedures and incisions for insertion and/or for tunneling, which increases the attendant risks of the catheterization procedure. Further, in the case of side-by-side placement of two catheter tubes through a single insertion site in a vessel, while minimizing the number of procedures, can present a potential for leakage between the catheter tubes at the point where the catheter tubes pass into the vessel.

However, catheters like the Tesio catheter assemblies provide catheters which are capable of independent movement within the vessel. Such catheters present several advantages over one catheter with multiple lumens. Because the individual tubes of a Tesio double catheter assembly are independently movable at their fluid outlets, it is possible to provide fluid intake and/or return flow around the entire circumference of the distal ends of the catheter tubes. In addition, if one tube becomes blocked, or otherwise requires replacement, it can be removed independently of the other tube. Further, the softer durometer of such catheters, which are typically made of a silicone or a similar material, reduces the risk of vessel wall damage. The 360 degree circumferential flow provides a more stable tube within the vessel, which is less likely to be suctioned against the vessel wall due to a pressure differential, as occasionally occurs in the use of some side-by-side multi-lumen catheters.

U.S. Pat. No. 5,718,692, issued to Schon, et al., ("the Schon catheter") describes a self-retaining double catheter system in which each catheter can be subcutaneously secured without the use of fabric tissue ingrowth cuffs or external suturing as a result of the placement of a retaining sleeve surrounding both individual catheters in a multiple catheter assembly to hold the catheters together at the location of the sleeve. The individual catheters are permanently linked in one portion by a hub for self-anchoring under the skin, as an alternative to requiring a fabric stabilizing cuff, such that such cuffs are optional. The distal ends are longitudinally prespaced by an appropriate distance to avoid recirculation. While this device requires only one incision, it requires two subcutaneous tunnels in order to facilitate the self-retaining feature. This catheter provides independently movable distal ends within the vessel and 360 degree circumferential flow in the manner of a standard Tesio. Further, since the retaining sleeve is located outside the vessel when in place to provide the self-retaining feature, at the point of entry into the vessel, the catheters are side-by-side in the manner of a standard Tesio catheter, and there still remains the potential risk of blood leakage between the catheters at the vessel site.

The idea of using a splitable catheter arose in 1983 U.S. Pat. No. 4,411,654 issued to Boarini et al, by using longitudinal lumens or grooves placed 180 degrees apart into the wall of the catheter during extrusion to provide lines of weakness from the proximal end to the distal end of the catheter.

U.S. Pat. No. 5,180,372 issued to Vegoe, et al. describe an improved placement catheter of the type having a longitudinal line of weakness whereby the catheter may be split longitudinally. The improved catheter is made with radiation cross-linked tubing to provide better splitability.

U.S. Pat. No. 5,947,953 issued to Ash et al. (2001) ("the split Ash catheter") discloses a splittable multiple catheter assembly that has a hub and at least two fully independent catheter tubes which are initially releasably joined together, for example, by a breakable membrane. A single subcutaneous tunnel may be used in inserting the catheter, and the catheter tubes are at least partially separated by splitting the catheter tubes prior to insertion into a vessel. As a result, the portions of the catheter within the vessel are capable of independently moving and having 360 degree circumferential flow from the distal portion of each tube. The catheter may be secured using standard securement means such as suturing, ingrowth or other available securement devices.

U.S. Pat. Application No. 2003/0153898 issued to Schon et al (2003) ("the Schoncath") discloses a multilumen catheter assembly, which includes a unitary portion and at least two distal end tubes extending distally from the unitary portion. The unitary portion includes an exterior having a generally round or oval shape in cross section and includes at least two distal end tubes of generally circular (or other) cross sectional shape extending longitudinally therethrough. The catheter assembly may be made by extruding a unitary tube having internal longitudinally extending lumens (of circular or other shape), then splitting the tube on its distal end portion to form distal end tubes. The tubes are then ground and polished, the finished tubes retaining, in combination, the generally oval cross sectional shape of the unitary extrusion, or the finished tubes can each be finished to a circular, or other, cross-sectional shape, or the finished tubes could include a combination of cross sectional shapes over its longitudinal length.

U.S. Pat. No. 6,524,302 which issued to Kelley (February, 2003), describes A multi-lumen catheter and method of manufacturing such a multi-lumen catheter having a plurality of individual catheter tubes. Each catheter tube has an outer surface, an inner surface and a lumen. The catheter tubes can be made of different thermoplastic materials. A mandrel is first inserted into the lumen of each catheter tube to provide support. The catheter tubes are then juxtaposed to each other in an arrangement. Importantly, the outer surface of one catheter tube is in contact with the outer surface of at least one other catheter tube in the arrangement. The arrangement of catheter tubes is then held in a sleeve and is advanced through the sleeve, and through a heating cylinder to fuse the outer surfaces of the catheter tubes. A cooling means is placed in the lumen of each catheter tube to prevent the inner surface of each catheter tube from melting.

There is a need in the art for a multiple catheter assembly and a need for making such a catheter assembly which can provide the advantages of the abovementioned multi-lumen catheters with respect to easy insertion through a single tunneling procedure and which can prevent the potential risk of leakage at the site of vessel entry, but which can still provide the advantage of multiple catheter assemblies with respect to independent movement within a vessel and good flow properties.

(B) Manufacturing Background

The SchonCath (U.S. Pat. Application No. 2003/0153898) invention includes methods for making the multilumen catheter. The method includes forming a unitary catheter tube having a proximal portion, a distal portion, and a distal end portion terminating in a distal end tip. The unitary catheter tube may be formed using any suitable heat molding process, including injection molding, expansion/compression molding, and extrusion. The unitary catheter tube is formed by extrusion through a die to form internal lumens, the lumens being substantially the same and substantially identical in size and configuration.

The unitary catheter tube, with internal longitudinally extending lumens, may also be formed by injection molding the tube around metal rods which have the shape of the internal lumens. The unitary catheter tube is then split longitudinally along the distal portion of the tube using a sharp edge such as a hot knife or razor blade for a pre-determined distance, depending upon the particular size desired for the catheter. The tube is preferably split as evenly as possible between the two lumens along an internal septum. Splitting the unitary catheter tube forms a first distal end tube and a second distal end tube. The second distal end tube can then be cut to size relative to the first distal end tube, if it is desired that one distal end tube be greater in length than the other. Separate lengths for the distal end tubes helps avoid recirculation of fluids entering and leaving the tubes within the area to be catheterized.

After the unitary catheter tube and the distal end tubes are formed, the exterior surface of the unitary catheter tube and the exterior surfaces of the distal end tubes are then ground and polished to a smooth surface. Radio frequency (RF) tipping can be used to provide the smooth surface. Radio frequency (RF) tipping uses RF energy to reheat an outer surface until there is some melting and then to polish the surface. Further, the unitary catheter tube and the distal end tubes could undergo radio frequency (RF) tipping on a mandrel, so that the tubes may be reshaped to have a generally circular transverse cross section both in the interior passageways (lumens) and on the exterior surfaces, if desired. Once the surfaces are shaped and smoothed, holes can then be formed in the distal end tubes, if desired, using techniques well known in the art. The number, size, shape, and spacing of the holes are as individually preferred, but some general and specific aspects have been described above. Portions of the split catheter can then be releasably attached, if desired, by bonding portions of exterior surfaces of the distal end tubes with a weak adhesive.

As an alternative to splitting the unitary catheter tube, after forming that tube, individual distal end tubes, which may be previously extruded or heat molded, may be fused onto the unitary catheter tube. The distal end tubes are formed such that they each have a respective longitudinal passageway (lumen) extending longitudinally therethrough, and may also be formed to include a plurality of holes prior to attachment to the distal end of the unitary catheter tube. Each formed distal end tube is then attached to the distal end of the unitary catheter tube by a suitable heat molding process, or by another form of attachment, such as adhesive, ultrasonic welding or other methods known in the art, such that the first passageway in the first distal end tube is in fluid communication with the first lumen of the unitary catheter tube and the second passageway in the second distal end tube is in fluid communication with the second lumen in the unitary catheter tube.

In one aspect of the invention, heat fusing is used to attach the distal end tubes, and such fusing may be carried out using heat applied to the unitary catheter tube and to the distal end tubing lengths in a female cavity mold to create a smooth fused portion where the tube and end tube lengths meet. Extension tubes may be provided either by extruding or molding the extension tubes initially when forming the unitary catheter tube using techniques similar to those used to form the distal end tubes as described above. However, it is preferred to attach the extension tubes to a proximal end of the unitary catheter tube using a hub. A hub is then molded around the proximal end of the unitary tube and the distal end of the proximally extending catheter tubes. Preferably, to maintain the unitary catheter and extension tubes in place, the hub mold either has cavities to receive the tubes, or metal rods inserted through the extension tubes and lumens within the formed unitary catheter portion, to retain the shape of the lumens and hold the tubes in place. A plurality of holes may also be provided to the distal end portions of the catheter tubes.

The Split Ash catheter (U.S. Pat. No. 6,190,349) invention, the multiple catheter assembly, includes extrusion of a first catheter that has an outer surface defining a first lumen. A second catheter has an outer surface defining a second lumen extending through the full length of the respective catheters. The lumens each have a generally semi-circular cross section. Accordingly, the first catheter has an outer surface defined by a rounded wall portion and a generally flat side surface, and the second catheter also has an outer surface defined by a rounded wall portion and a generally flat side surface, as viewed in cross section. The flat side surfaces face each other. The generally flat side surfaces do not touch each other, but are very close. Also, the lumens and respective rounded wall portions and generally flat side surfaces are identical to each other so that the cannulating portion of the catheter assembly has a generally circular cross section. The catheter assembly includes a splitable membrane which extends longitudinally between and joins the opposite, generally flat side surfaces, of the first and second catheters. It is preferred that the membrane extends between the central line of the flat side surfaces for dimensional stability. However, the membrane could extend between edges of the side surfaces or between other regions of the flat side surfaces or rounded wall portions.

The membrane performs multiple functions. First, the membrane joins the first and second catheters so that the catheters can be easily manipulated, particularly along the section of the catheters where the membrane is unbroken. If the membrane is completely intact, the catheters can be manipulated as a single catheter. Second, the membrane allows the first and second catheters to be at least partially longitudinally split apart from each other without damaging the outer surfaces of either of the first or second catheters thereby allowing independent movement of the split end regions in the vessel or other area to be catheterized.

The membrane is constructed to split easily when the first and second catheters are forcibly separated from each other. The membrane has a cross-sectional width that at its thinnest portion is a very small fraction of the outer diameter of the catheter assembly to facilitate easy tearing. The membrane is constructed of a material which will tear before the forces exerted on the outer surfaces of either of the first or second catheters reach a level sufficient to cause damage thereto. However, the membrane material should be sufficiently strong to resist tearing during normal handling of the assembly. The membrane has a cross-sectional length which is also a small fraction of the outer diameter of catheter assembly. The cross-sectional length also defines the distance between the generally flat side surfaces. The cross-sectional distance is preferably small to maintain an overall generally circular cross section for the unseparated section of the catheter assembly and to facilitate handling of the unseparated section of the catheter assembly in the cannulation portion. The cannulation portion is joined to the extension tube portion by a hub.

Kelly catheter (U.S. Pat. No. 6,524,302) and method for manufacturing cannot control the surface or the size of the end result fused tube as the cross-section of the multi-lumen catheter has an outer periphery with at least three distinct lobes, with each distinct lobe corresponding to one of said fused tubes and not a rounded outer surface area. Also, an additional lumen is created from the outer surfaces of the three fused catheter tubes.

SUMMARY OF THE INVENTION

The present invention relates generally to multitube catheter assemblies and includes two or more tubes fused together to form one catheter tube shaft. Each tube has at least one lumen extending longitudinally through the catheter from its distal end to its proximal end. The tubes are fused together by use of heat and pressure.

The multitube catheter assemblies have distal split independent free floating tip ends, a stepped tip end, or a tapered tip end for positioning within an area to be catheterized.

The lumens of the multitube catheter are fully circular where they extend all through the distal end, the catheter main stem and the proximal end of the extension part. The presented multitube catheters are to be used in any medical field where access to the central venous system is required like haemodialysis, haemofiltration, plasma exchange, chemotherapy infusion, etc.

The way of fusion and the degree of heat and pressure applied, can allow the catheter tubes to be releasable joined and longitudinally split from each other. The tubes are fused together by use of heat sensitive tube slides over the tubes while metallic mandrels are passed through each tube lumen to protect the lumens during fusion. The heat sensitive tube will generate pressure once heat is applied. Continual heating will melt/reshape the catheter tubes inside the heat sensitive tube. After cooling the heat sensitive tube is removed around the catheter tube. The metallic mandrels are then pulled back. The tubes, forming the one catheter tube are separated at each end. The end result is a multitube tube catheter that has a distal split end.

In one aspect of the present invention, the assembly includes the fusion between a first tube and a shorter second tube to form one catheter tube. Each tube has at least one lumen extending longitudinally through the catheter. The way of fusion and the degree of heat and pressure applied, allow the catheter tubes to be unreleasably joined. The tubes are fused together by use of heat sensitive tube slides over the tubes while metallic mandrels are passed through each tube lumen to protect the lumens during fusion. The heat sensitive tube will generate pressure once heat is applied. Continual heating will melt/reshape the catheter tubes inside the heat sensitive tube. After cooling, the heat sensitive tube is removed around the catheter tube. The metallic mandrels are then pulled back. The end result is a multitube tube catheter has a distal stepped end.

In another aspect of the present invention, the assembly includes fusion between two or more tubes fused together to form one catheter tube shaft. Each tube has at least one lumen extending longitudinally through the catheter from its distal end to its proximal end. The way of fusion and the degree of heat and pressure applied, allow the catheter tubes to be unreleasably joined. The tubes are fused together by use of heat sensitive tube slides over the tubes while metallic mandrels are passed through each tube lumen to protect the lumens during fusion. The heat sensible tube will generate pressure once heat is applied. Continual heating will melt/reshape the catheter tubes inside the heat sensitive tube. After cooling, the heat sensitive tube is removed around the catheter tube. The metallic mandrels are then pulled back. The distal end of the fused united tube has a tapered tipped. The end result is a multitube tube catheter that has a distal tapered tip end.

In another aspect of the present invention, the catheter tube stem, the distal end tubes, and the lumens, can also have a different shape or configuration at different points along a respective longitudinal length of each.

In another aspect of the present invention, through using the art of a heat shrink tube, the outer wall of the catheter stem tube, the outer wall of the distal end tubes, and the lumens, can have various shapes in cross section, such as, but not limited to, a circular, semi-circular, or oval shape.

In another aspect of the present invention, the first and the second distal end tubes have an outer wall with half-circular cross section, that can be reformed to a circular wall by using the same principles of the current invention by applying a heat shrink tube over each of the distal tubes.

The present invention also provides a method for making a multitube catheter assembly, by fusing two or more tubes together by use of heat sensitive tube slides over the tubes while metallic mandrels are passed through each tube lumen to protect the lumens during fusion. The heat sensitive tube will generate pressure once heat is applied. Continual heating will melt/re-shape the catheter tubes inside the heat sensitive tube while the latter will not be affected due to its high melting temperature. After cooling, the heat shrink tube is removed around the fused catheter tubes, the metallic mandrels are pulled back, forming the one catheter tube.

In another aspect of the invention and method, two or more tubes are fused together by use of an elastic tube stretched and slid over the tubes while metallic mandrels are passed through each tube lumen to protect the lumens during fusion. The elastic tube will compress the catheter tubes. Continual heating will melt/re-shape the catheter tubes inside the silicon tube while the latter will not be affected due to its high temperature resistance. The elastic tube will compress over the melted catheter tubes. After cooling, the elastic tube is slid back from the fused catheter tubes, the metallic mandrels are pulled back forming the one catheter tube. The elastic tube can be silicon, rubber or equivalent material.

In another aspect of the invention, a cuff or similar device is applied to the catheter stem. The absence of a connector or a hub between the catheter shaft and extension line allows the catheter to be tunneled in both directions, i.e. place and position the catheter tip inside the vessel and then tunnel the subcutaneous part OR tunnel the subcutaneous part, then advance the catheter tip in the vessel. A catheter luer end is to be provided separately (to be assembled after tunneling) or pre-attached to the extension lines.

In another aspect of the invention, the absence of a connector or a hub between the catheter shaft and extension line allows the catheter to be advanced and positioned to any desirable length, then fixed with any fixation devices.

In another aspect of the invention, the multitube catheter assembly extension legs (lines) may end in a fixed or removable luer end.

BRIEF DESCRIPTION OF THE DRAWINGS & PICTURES

The accompanying drawings, which are incorporated herein and constitute part of this specification, illustrate the presently preferred embodiments of the invention, and, together with the general description given above, and the detailed description given below, serve to explain the features of the invention in the drawings.

DETAILED DESCRIPTION OF THE INVENTION

Figures 1, 1A:
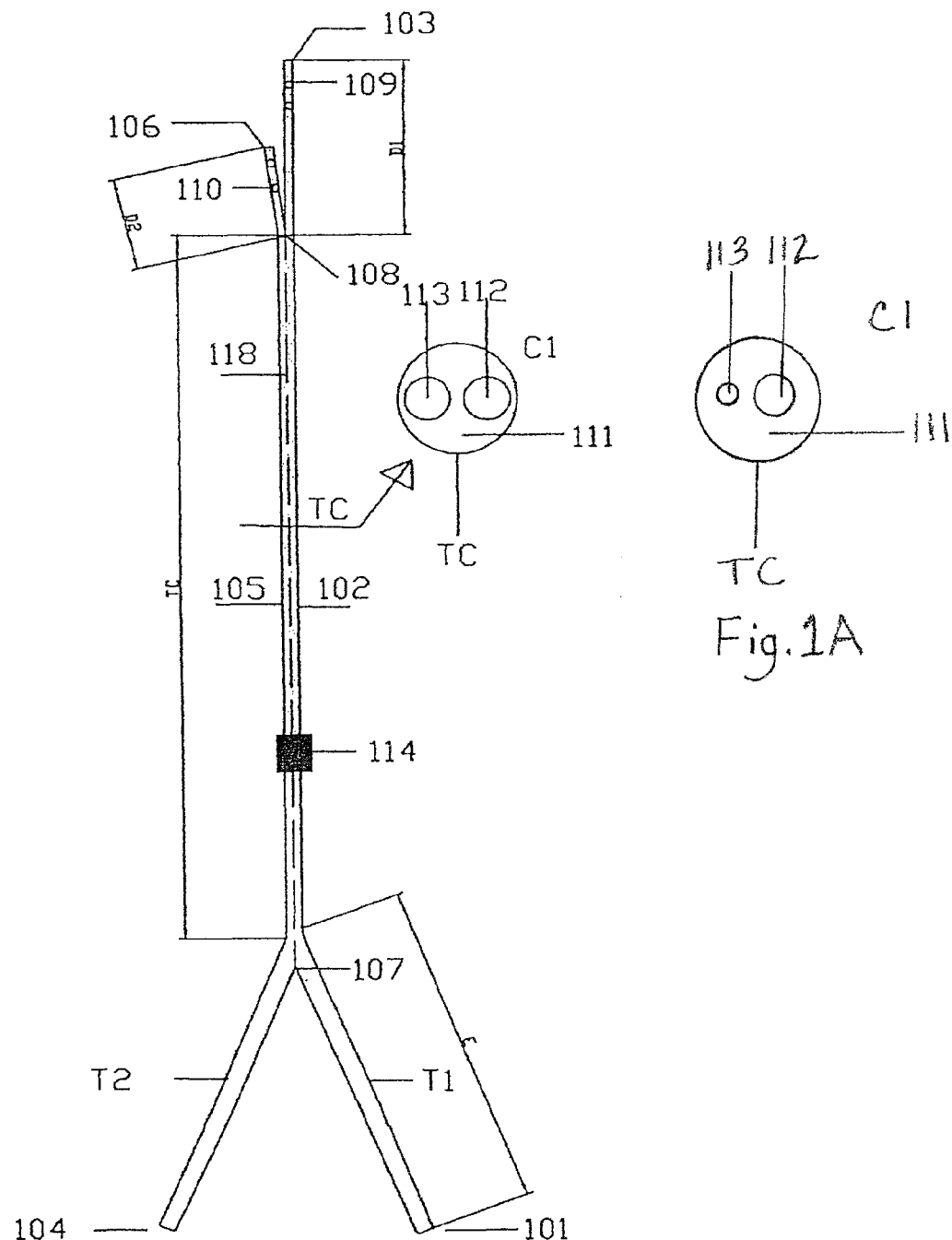
FIG. 1 is a top plan view of a catheter assembly according to the first embodiment of the present invention.

In describing the embodiments of the invention illustrated in the drawings, specific terminology will be used for the sake of clarity. However, the invention is not intended to be limited to the specific terms so selected, it being understood that each specific term includes all technical equivalents operating in similar manner to accomplish similar purpose. It is understood that the drawings are not drawn exactly to scale. In the drawings, similar reference numbers are used for designating similar elements throughout the several figures.

The following describes particular embodiments of the invention. However, it should be understood, based on this disclosure, that the invention is not limited to the embodiments detailed herein. Generally, the following disclosure refers to dual or triple lumen catheter assemblies, although catheter assemblies having more lumens and/or distal end tubes are within the scope of the invention. Further, the methods described below for making the catheter assemblies of the present invention are also applicable to making catheter assemblies having more than two lumens and/or distal end tubes. It is only for reasons of convenience that the following description refers to two or three lumen embodiments of the present invention.

The multitube catheter assemblies of the present invention are inserted into an area of a body of a patient to be catheterized for removing and introducing fluids to the body. The catheter assemblies of the present invention are secured to a fixed location in or on the patient body, such as a subcutaneous area, before the catheter assembly is properly inserted and positioned in the area to be catheterized. This method is particularly preferred for long term catheterization. Alternatively, in short term catheterization, the catheter assemblies of the present invention may be secured to an external surface of the body before or after the catheter assembly is properly inserted and positioned in the area to be catheterized.

The multitube catheter assemblies of the present invention can be adapted for use in various applications in which bodily fluids, medicaments, or other solutions are introduced into and removed from the body, such as perfusion, infusion, plasmapheresis, hemodialysis, chemotherapy, and the like. The catheter assemblies of the present invention are particularly suitable for chronic hemodialysis and apheresis. The area to be catheterized is preferably a blood vessel, such as an internal jugular vein, but may be any suitable area within the body. Other areas in which the catheter assemblies may be used include other blood vessels, including the femoral and subclavian veins, any cavity, and other areas of the body including intra-abdominal, sub-diaphragmatic and sub hepatic areas. It is understood that the above-referenced areas are exemplary, and that the catheter assemblies of the present invention may be used to remove or introduce fluids to various areas to be catheterized.

The embodiments of the present invention shown in the figures are particularly useful for intake, or removal, of blood to be purified from a blood vessel, such as the internal jugular vein, and introduction of purified blood into the same vessel. The blood can be purified by any suitable hemodialysis apparatus attached in communication with lumens of the disclosed catheter assemblies. The catheter assemblies of the present invention may also be used to introduce medication or other fluids, including glucose or saline solutions, into the body.

For purposes of describing the embodiments of the present invention shown in the figures, the catheter assemblies will be described with respect to an application of hemodialysis and or as channeling to the venous system. However, it is understood that the catheter assemblies of the present invention can be configured and adapted, by increasing or decreasing a size (diameter or length) and/or number of distal end tubes and/or lumens in the respective catheter assembly, so that the catheter assembly can be beneficially used for other medical applications in which fluids are introduced into and/or removed from the body.

A First Embodiment

FIG. 1 illustrates one embodiment of the present invention, where a catheter assembly has at least two lumens. The illustration of two lumens is exemplary, and the scope of the invention encompasses catheters having more than two lumens.

The catheter assembly includes first tube T1 which has a proximal end 101 and a distal end 103. The catheter assembly includes second tube T2 which has a proximal end 104 and a distal end 106. The first tube T1 and the second tube T2 are united (fused) at catheter shaft TC as a result of fusion of a portion 104 of first tube T1 and the 105 of second tube T2.

The catheter assembly can be provided (manufactured) so that the first distal end tube D1 and the second distal end tube D2 are splitable (releasably attached) or separate at their respective distal ends. Splitable is defined as releasably attached, meaning the first and the second distal end tubes D1 and D2 are fused, or otherwise attached, so that only minor force is necessary to pull apart, or split, the fuses along the imaginary line 118.

The first tube T1 and second tube T2 are split at the end of the catheter tube fused part TC at the point 108 and form free floating distal parts D1 & D2.

The multilumen catheter assembly includes a first lumen 112 and a second lumen 113 extending longitudinally therethrough as illustrated at C1.

The first lumen 112 is continuous with and through the floating distal part D1, the catheter shaft TC and first extension tube E1. The second lumen 113 is continuous with and through the floating distal part D2, the catheter shaft TC and first extension tube E2. The first and the second extension tubes E1 and E2 lead to a proximal end of the catheter assembly, through which the materials entering and or exiting the patient enter and/or exit the catheter assembly. The words "proximal" and "distal" refer to directions away from and closer to, respectively, the inserted end of the catheter assembly.

The exterior of the catheter shaft TC is smooth and rounded without ridges or grooves.

As shown in the cross-section C1 of the catheter shaft TC, the outer surface of the catheter shaft TC is generally rounded in shape (outer configuration), C1 illustrating in cross-section a generally round shaped outer wall, with the first and the second lumens 112, 113 having a circular cross-section. Catheter shaft TC can have various shapes, such as, but not limited to, circular, semi-circular or oval. Also, the lumen cross section can have various shapes, such as, but not limited to, circular, semi-circular or oval.

A cuff 114 may and may not be located at a point along the catheter shaft TC. Cuffs are known in the art and provide a surface onto which internal tissue may adhere to stabilize the catheter assembly within the patient.

In the above mentioned embodiments, it is noted that the proximal ends 101, 104 may occur at different locations in various catheters. It is within the scope of the present invention to incorporate, in the dimensional aspects of length disclosed above, all locations where the proximal ends 101, 104 could be said to occur in catheters known in the art, disclosed herein, or to be developed.

The smooth generally round exterior surface of the catheter shaft TC passes through and remains positioned at a vessel wall insertion site during insertion of the catheter assembly into a patient. A vessel wall seals quite well around the smooth, round exterior surface of the catheter shaft TC, as shown in cross-section C1. Since the exterior of the catheter shaft TC provides a good seal at the insertion site, the risk of blood loss around the catheter assembly at the insertion site is minimized.

The first and the second distal end tubes D1, D2 extend distally from the catheter shaft TC at the split point 108. The first and the second distal end tubes D1, D2 have outer surfaces continuous with the outer wall of the unitary catheter shaft TC, and are capable of independent movement when split from one another.

The first and the second distal end tubes D1, D2 are defined by circular outer walls. The first and the second lumens 112, 113 are circular.

The first and the second lumens 112, 113 are always circular since circular cross sections are most conducive to fluid flow properties. However, other shapes such as D-shaped passageways and/or lumens, oval, triangular, square, elliptical, kidney-bean shaped passageways and/or lumens, or other configurations are also within the scope of the invention. Further, while the catheter tubes T1, T2, the distal end tubes D1, D2, the lumens 112, 113 and the proximal end tubes E1, E2 are preferably identical in cross section, it is within the scope of the invention to vary the size, shape and/or configuration such that smaller distal end tubes and/or lumens, or varying types of lumens and distal end tubes may be used for other applications, such as an addition of a third, smaller lumen, and corresponding distal end tube for introduction of medication.

In addition to an L1 & L2 distal end opening, the first and the second distal end tubes D1, D2 may or may not have a plurality of side holes 109, 110 extending through exterior surfaces of the distal end tubes D1, D2 to the first and the second lumens 112, 113. The side holes 109, 110 provide additional or alternative flow paths. The side holes 109, 110 can be arranged circumferentially and helically around the distal end tubes D1, D2 to provide optimal flow properties, and to avoid suctioning of the distal tubes against an area to be catheterized, such as a vessel wall. The side holes 109, 110 can be of various shape, but are typically circular or oval, or of some combination thereof and may also vary in number between the shorter and longer of the distal end tubes D1, D2.

A Second Embodiment

Figure 2:
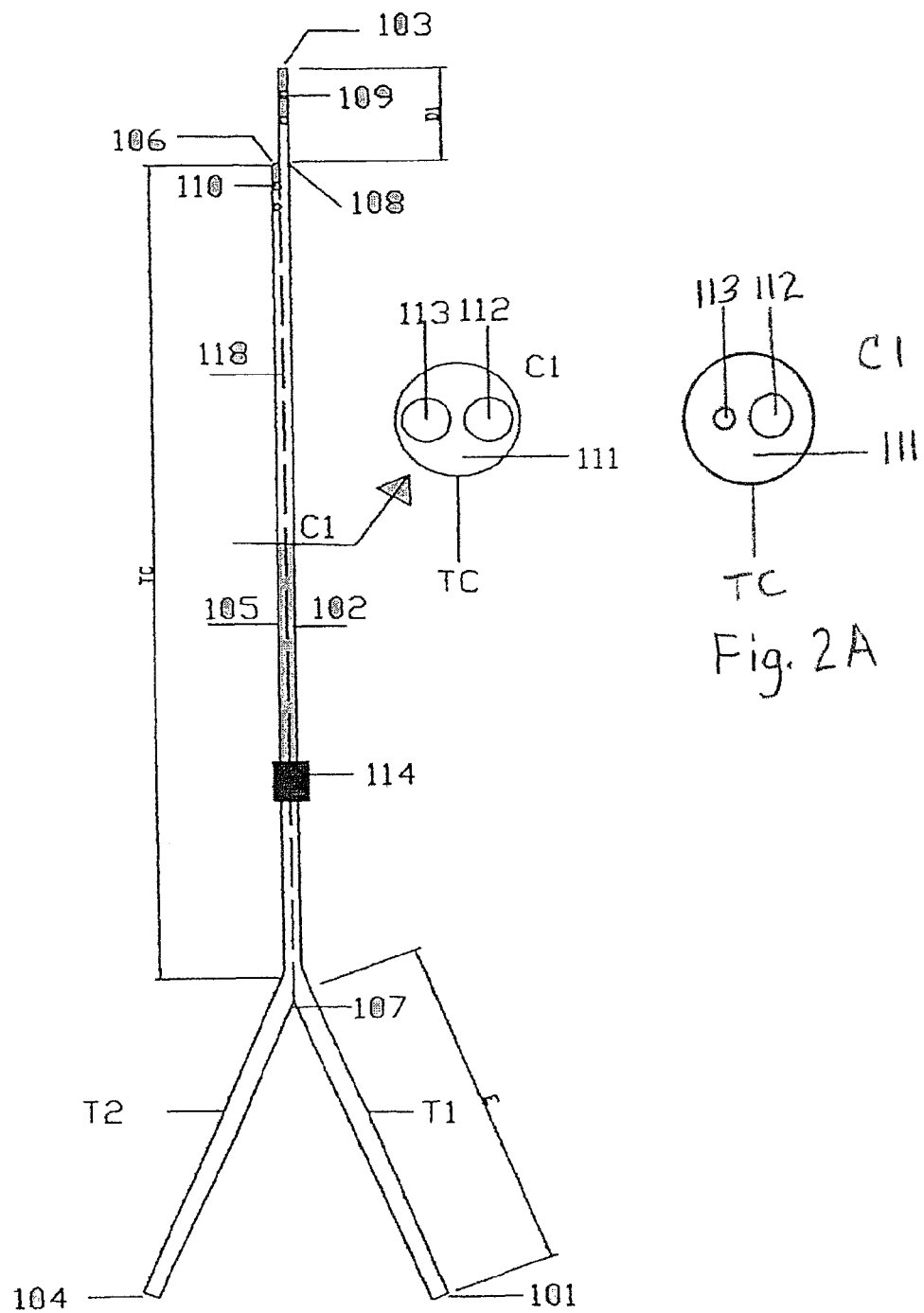
FIG. 2 is a top plan view of a catheter assembly according to the second embodiment of the present invention.

FIG. 2 illustrates another embodiment of the present invention, where a catheter assembly has at least two lumens. The illustration of two lumens is exemplary, and the scope of the invention encompasses catheters having more than two lumens.

The catheter assembly includes first tube T1 which has a proximal end 101 and a distal end 103. The catheter assembly includes a shorter second tube T2 which has a proximal end 104 and a distal end 106. The first tube T1 and the second tube T2 are united (fused) at catheter shaft TC as a result of fusion of a portion 104 of first tube T1 and the 105 of second tube T2.

The catheter assembly can be provided (manufactured) so that the first distal end tube D1 is extending distally beyond the second tube distal end 106.

The multilumen catheter assembly includes a first lumen 112 and a second lumen 113 extending longitudinally therethrough as illustrated at C1.

The first lumen 112 is continuous with and through the first tube T1 from the distal end 103 of the floating distal part D1, the catheter shaft TC and first extension tube E1. The second lumen 113 is continuous with and through the second tube T2 from the distal end 106 of the second tube T2, the catheter shaft TC and first extension tube E2. The first and the second extension tubes E1 and E2 lead to a proximal end of the catheter assembly, through which the materials entering and or exiting the patient enter and/or exit the catheter assembly. The words "proximal" and "distal" refer to directions away from and closer to, respectively, the inserted end of the catheter assembly.

The exterior of the catheter shaft TC is smooth and rounded without ridges or grooves.

As shown in the cross-section C1 of the catheter shaft TC, the outer surface of the catheter shaft TC is generally rounded in shape (outer configuration), C1 illustrating in cross-section a generally round shaped outer wall, with the first and the second lumens 112, 113 having a circular cross-section. Catheter shaft TC can have various shapes, such as, but not limited to, circular, semi-circular or oval. Also, the lumen cross section can have various shapes, such as, but not limited to, circular, semi-circular or oval.

A cuff 114 may or may not be located at a point along the catheter shaft TC. Cuffs are known in the art and provide a surface onto which internal tissue may adhere to stabilize the catheter assembly within the patient.

In the above mentioned embodiments, it is noted that the proximal ends 101, 104 may occur at different locations in various catheters. It is within the scope of the present invention to incorporate, in the dimensional aspects of length disclosed above, all locations where the proximal ends 101, 104 could be said to occur in catheters known in the art, disclosed herein, or to be developed.

The smooth generally round exterior surface of the catheter shaft TC passes through and remains positioned at a vessel wall insertion site during insertion of the catheter assembly into a patient. A vessel wall seals quite well around the smooth, round exterior surface of the catheter shaft TC, as shown in cross-section C1. Since the exterior of the catheter shaft TC provides a good seal at the insertion site, the risk of blood loss around the catheter assembly at the insertion site is minimized.

The distal end tubes D1 extend distally from the catheter shaft TC at the point 108. The distal end tubes D1 has outer surfaces continuous with the outer wall of the unitary catheter shaft TC, and are capable of independent movement.

The first distal end tubes D1 is defined by a circular outer wall. The first and the second lumens 112, 113 are circular.

The first and the second lumens 112, 113 are always circular since circular cross sections are most conducive to fluid flow properties. However, other shapes such as D-shaped passageways and/or lumens, oval, triangular, square, elliptical, kidney-bean shaped passageways and/or lumens, or other configurations are also within the scope of the invention. Further, while the catheter tubes T1, T2, the distal end tube ED, the lumens 112, 113 and the proximal end tubes E1, E2 are preferably identical in cross section, it is within the scope of the invention to vary the size, shape and/or configuration such that smaller distal end tubes and/or lumens, or varying types of lumens and distal end tubes may be used for other applications, such as an addition of a third, smaller lumen, and corresponding distal end tube for introduction of medication.

The assembly according to the second embodiment, in addition to an L1 & L2 distal end opening, may or may not include a plurality of side holes 109 extending through exterior surfaces of the distal end tubes D1, to the first lumen 112. A second set of side holes 110 extending through exterior surfaces of the distal end of tube 105, to the second lumen 113. The side holes 109, 110 provide additional or alternative flow paths. The side holes 109, 110 can be of various shapes, but are typically circular or oval, or some combination thereof.

A Third Embodiment

Figure 3:
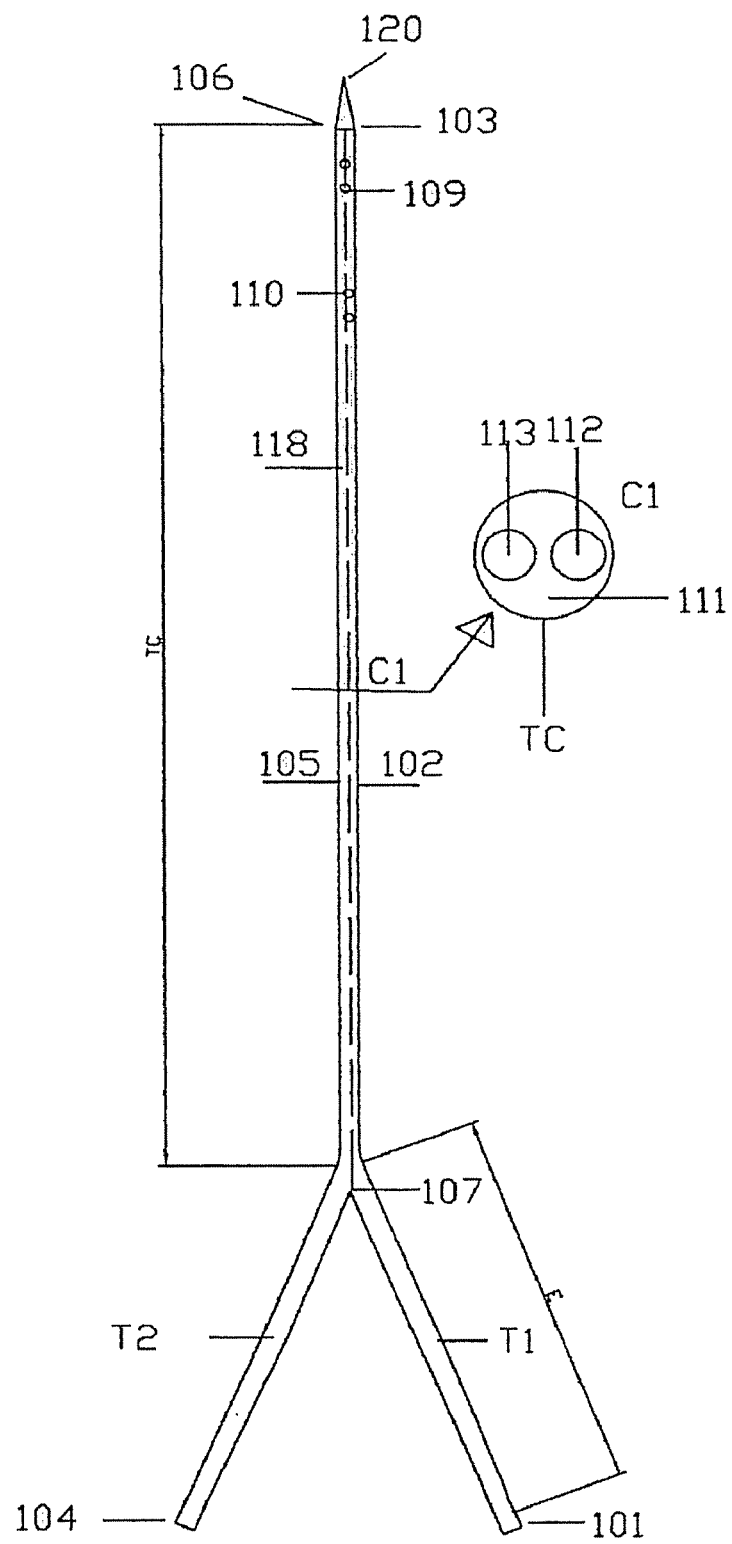
FIG. 3 is a top plan view of a catheter assembly according to the third embodiment of the present invention.

FIG. 3 illustrates another embodiment of the present invention, where a catheter assembly has at least two lumens. The illustration of two lumens is exemplary, and the scope of the invention encompasses catheters having more than two lumens.

The catheter assembly includes first tube T1 which has a proximal end 101 and a distal end 103. The catheter assembly includes a second tube T2 which has a proximal end 104 and a distal end 106. The first tube T1 and the second tube T2 are united (fused) at catheter shaft TC as a result of fusion of a portion 104 of first tube T1 and the 105 of second tube T2.

The catheter assembly can be provided (manufactured) so that the first tube T1 and the second tube T2 are fused along a portion extending from the point 107 to the end of both tubes 103, 106 so as to have a common distal end.

The assembly according to the third embodiment includes tipping of the distal end of the catheter shaft TC to form a distal catheter tip 120.

The multilumen catheter assembly includes a first lumen 112 and a second lumen 113 extending longitudinally therethrough as illustrated at C1.

The first and second lumen 112, 113 are continuous with and through the first and second tube T1, T2 from the distal end 103, 106, the catheter shaft TC and first and second extension tube E1, E2. The first and the second extension tubes E1 and E2 lead to a proximal end of the catheter assembly, through which the materials entering and or exiting the patient enter and/or exit the catheter assembly. The words "proximal" and "distal" refer to directions away from and closer to, respectively, the inserted end of the catheter assembly.

The exterior of the catheter shaft TC is smooth, rounded without ridges or grooves.

As shown in the cross-section C1 of the catheter shaft TC, the outer surface of the catheter shaft TC is generally rounded in shape (outer configuration), C1 illustrating in cross-section a generally round shaped outer wall, with the first and the second lumens 112, 113 having a circular cross-section. Catheter shaft TC can have various shapes, such as, but not limited to, circular, semi-circular or oval. Also lumen cross section can have various shapes, such as, but not limited to, circular, semi-circular or oval In the above mentioned embodiments, it is noted that the proximal ends 101, 104 may occur at different locations in various catheters. It is within the scope of the present invention to incorporate, in the dimensional aspects of length disclosed above, all locations where the proximal ends 101, 104 could be said to occur in catheters known in the art, disclosed herein, or to be developed.

The smooth generally round exterior surface of the catheter shaft TC passes through and remains positioned at a vessel wall insertion site during insertion of the catheter assembly into a patient. A vessel wall seals quite well around the smooth, round exterior surface of the catheter shaft TC, as shown in cross-section C1. Since the exterior of the catheter shaft TC provides a good seal at the insertion site, the risk of blood loss around the catheter assembly at the insertion site is minimized.

The first and the second lumens 112, 113 are always circular since circular cross sections are most conducive to fluid flow properties. However, other shapes such as D-shaped passageways and/or lumens, oval, triangular, square, elliptical, kidney-bean shaped passageways and/or lumens, or other configurations are also within the scope of the invention. Further, while the catheter tubes T1, T2, the lumens 112, 113 and the proximal end tubes E1, E2 are preferably identical in cross section, it is within the scope of the invention to vary the size, shape and/or configuration such that smaller distal end tubes and/or lumens, or varying types of lumens and distal end tubes may be used for other applications, such as an addition of a third, smaller lumen and corresponding distal end tube for introduction of medication.

A plurality of side holes 109, 110 extending through exterior surfaces of tubes 102, 105, to the first and second lumens 112, 113. The side holes 109, 110 provide additional or alternative flow paths. The side holes 109, 110 can be of various shapes, but are typically circular or oval, or some combination thereof.

A cuff 114 may or may not be located at a point along the catheter shaft TC. Cuffs are known in the art and provide a surface onto which internal tissue may adhere to stabilize the catheter assembly within the patient.

The catheter assembly according to the various embodiments may be secured to patient skin by a fixation device.

The catheter assembly according to the various embodiments may incorporate a hub secured or over molded over point 107.

The present invention further includes methods for making the multilumen catheter assemblies described above.

The fusion parameter settings allow the catheter tube either to be releasably joined to allow the tubes to be longitudinally split from each other or non releasably joined.

The present invention also provides a method for making a multitube catheter assembly, by fusing two or more tubes together by use of heat sensitive tube slides over the tubes while metallic mandrels are passed through each tube lumen to protect the lumens during fusion. The heat sensitive tube will generate pressure once heat is applied. Continual heating will melt/re-shape the catheter tubes inside the heat sensitive tube while the latter will not be affected due to its high melting temperature. After cooling, the heat shrink tube is removed around the fused catheter tubes, the metallic mandrels are pulled back, forming the one catheter tube.

Figure 4:
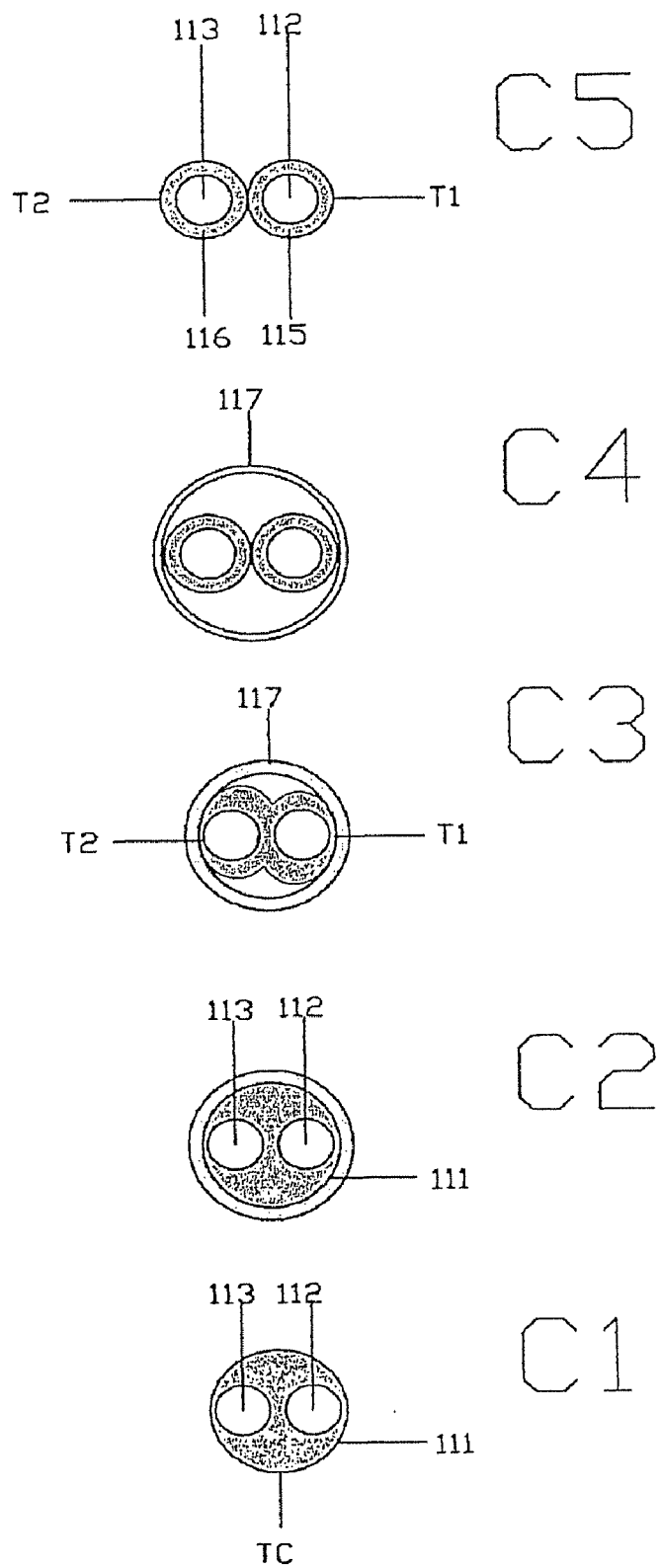
FIG. 4 is an enlarged view of catheter tube cross sectional changes during different steps of the fusion process.

As FIG. 4 illustrates, the catheter tubes T1, T2 cross section changes during the fusion process. According to C5, the first tube T1 and the second tube T2 has a general round outer surface and circular lumen 112, 113 and a wall 115, 116. C4 illustrates the presence of the heat sensitive tube 117 slide over the first and second tube T1, T2. The heat sensitive tube 117 contracts and generates pressure once heat is applied. Continual heating will melt/re-shape the catheter tubes T1, T2 inside the heat sensitive tube 117 while the latter will not be affected due to its high melting temperature. At C3, continual heating melts the wall 115, 116 of the first and second tube T1, T2. At C2, The wall 115, 116 fuse together forming one wall 111 defining the catheter tube TC around the catheter lumen 112, 113. Catheter lumens 112, 113 are protected during the fusion process by the presence of a round mandrel with a definite size inside each of them. At C1, after cooling, the heat sensitive tube 117 is removed from the formed TC. The metallic mandrels are pulled back, the catheter shaft tube TC is formed with the wall 111 around the catheter lumens 112, 113.

I claim:

1. A multitube catheter assembly comprising: a plurality of tube catheters, each having a proximal opening, a distal opening and outer surface defining a lumen extending longitudinally therethrough between the respective distal and proximal openings, said lumens each having a length, the tube catheters being non-concentric with at least one of said lumens being circular throughout the length between said respective distal and proximal openings; each lumen being independent from each other; wherein a portion of the outer surface of one tube catheter is fused to at least a portion of the outer surface of at least one other tube catheter to form a fused bundle comprising a generally circular outer wall comprising fused material, such that when viewed in transverse cross section, the fused bundle comprises a generally circular outside configuration defined by said wall; wherein the lumens each have a diameter when viewed in transverse cross section; an outer boundary of said lumens being formed from fused material, said fused material being generally radially, and circumferentially distributed within a region corresponding to the outer wall and a region outside the lumen diameter, such that each lumen is substantially surrounded by fused material.

2. The multitube catheter assembly according to claim 1, wherein the lumens are identical in transverse cross section.

3. The multitube catheter assembly according to claim 1, wherein the plurality of tube catheters is comprised of a shorter tube and a longer tube, the distal opening of said shorter tube being proximal to the distal opening of said longer tube, said distal openings having a distance between them, said distance being sufficient to prevent recirculation of a first fluid passing through the distal opening of the shorter tube in a first flow direction and second fluid passing through the distal opening of the longer tube in a second flow direction, the first and second flow directions being different.

4. The multitube catheter assembly according to claim 3, wherein the outer surfaces of the shorter and longer tubes are unreleasably joined.

5. The multitube catheter assembly according to claim 4, wherein a portion of said longer tube has a greater circular cross section than a circular cross section of said shorter tube.

6. The multitube catheter assembly according to claim 4, wherein said shorter tube is dedicated to receive a withdrawal fluid, and wherein said longer tube is dedicated to an infusion fluid.

7. The multitube catheter assembly according to claim 1, wherein the outer surfaces of the catheter tubes are unreleasably joined.

8. The multitube catheter assembly of claim 1 wherein the assembly is capable of being fixed to a patient's skin.

9. The multitube catheter assembly of claim 1 further comprising a cuff.

10. The multitube catheter assembly of claim 1 wherein the tube catheters are releasably joined.

11. The multitube catheter assembly of claim 1 wherein the tube catheters are identical in transverse cross section.

12. The multitube catheter assembly according to claim 1 wherein said fused material comprises once melted material from said plurality of tube catheters.

13. The multitube catheter assembly according to claim 1 wherein the catheter tubes are non-conjoined at the distal opening.

14. The multitube catheter assembly according to claim 1 wherein the catheter tubes are conjoined at the distal opening.

15. The multitube catheter assembly according to claim 1, wherein said assembly is comprised of an assembly distal end and an assembly proximal end, wherein the assembly distal end is tapered so as to form a tapered tip and wherein the assembly proximal end is comprised of catheter extension legs.

16. The multitube catheter assembly according to claim 15, wherein said tapered tip is comprised of an opening for at least one of the tubes.

17. The multitube catheter assembly of claim 15 wherein the extension legs are further comprised of a fixed or removable luer end.

18. The multitube catheter assembly according to claim 15, wherein one or more of the tubes have side openings near the assembly distal end.

* * * * *